Figure 1:
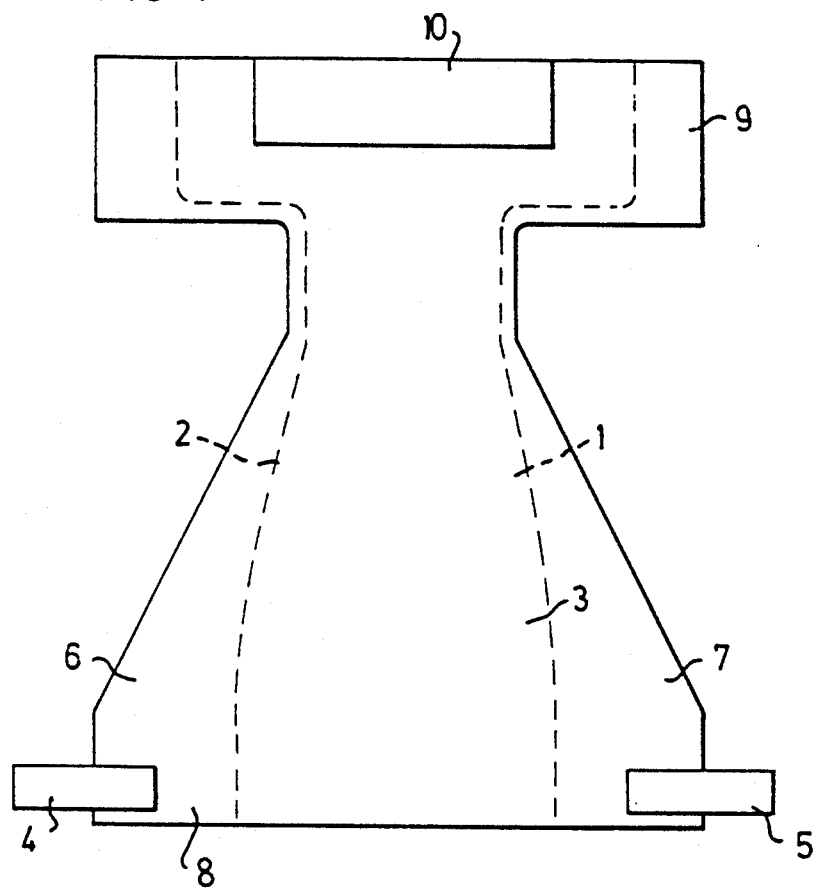

United States Patent [19]
Widlund

[11] Patent Number: 5,236,429
[45] Date of Patent: * Aug. 17, 1993

[54] DISPOSABLE DIAPER

[75] Inventor: Leif U. R. Widlund, Mölndal, Sweden

[73] Assignee: Molnlycke AB, Goteborg, Sweden

[*] Notice: The portion of the term of this patent subsequent to Jun. 18, 2008 has been disclaimed.

[21] Appl. No.: 703,735

[22] Filed: May 21, 1991

Related U.S. Application Data

[60] Division of Ser. No. 281,457, Dec. 8, 1988, Pat. No. 5,024,672, which is a continuation of Ser. No. 51,192, May 18, 1987, abandoned, which is a continuation of Ser. No. 844,268, Feb. 26, 1986, abandoned, and a continuation of Ser. No. 543,894, Oct. 20, 1983, abandoned.

[30] Foreign Application Priority Data

Oct. 25, 1982 [SE] Sweden .................... 8206042-7

[51] Int. Cl.⁵ ................. A61F 13/15; A61F 13/20
[52] U.S. Cl. ................... 604/390; 604/389; 604/385.1
[58] Field of Search .............. 604/390, 385.1, 389, 604/386, 390, 392, 386, 387

[56] References Cited

U.S. PATENT DOCUMENTS

| | | | |
|---|---|---|---|
| 2,834,347 | 5/1958 | Connally | 604/389 |
| 3,561,446 | 2/1971 | Jones, Sr. | |
| 3,610,244 | 10/1971 | Jones, Sr. | |
| 3,730,184 | 5/1973 | Mesek | |
| 3,777,758 | 12/1973 | Mesek et al. | |
| 3,867,940 | 2/1975 | Mesek et al. | 604/390 X |
| 4,024,867 | 5/1977 | Mesek | |
| 4,210,144 | 7/1980 | Sarge, III et al. | 604/390 X |
| 4,296,750 | 10/1981 | Woon et al. | 604/389 X |
| 4,436,520 | 3/1984 | Lipko et al. | |
| 4,643,730 | 2/1987 | Chen et al. | 604/390 |
| 4,710,190 | 12/1987 | Wood | 604/390 X |
| 5,024,672 | 6/1991 | Widlund | 604/390 |

FOREIGN PATENT DOCUMENTS

| | | | |
|---|---|---|---|
| 0455663 | 4/1949 | Canada | 604/389 |
| 3338201 | 4/1984 | Fed. Rep. of Germany | 604/389 |
| 1444433 | 7/1976 | United Kingdom | 604/390 |

Primary Examiner—David Isabella
Assistant Examiner—Elizabeth M. Burke
Attorney, Agent, or Firm—Young & Thompson

[57] ABSTRACT

A disposable diaper which can be put on by means of pressure-adhesive tape. For loosening and refastening the fastening tape tabs, the diaper is provided in the region for fastening the tape tabs with a non-elastic plastic strip, suitably of polyester.

3 Claims, 2 Drawing Sheets

DISPOSABLE DIAPER

This application is a division, of application Ser. No. 07/281,457, filed Dec. 8, 1988, now U.S. Pat. No. 5,024,672 which is a continuation of Ser. No. 07/051,192, filed May 18, 1987, now abandoned, which is a continuation of Ser. No. 06/844,268, filed Feb. 26, 1986, now abandoned, and a continuation of Ser. No. 06/543,894, filed Oct. 20, 1983, now abandoned.

Arrangement in a Disposable Diaper

The present invention relates to a device in a disposable diaper put on by means of pressure adhesive tape, comprising a liquid permeable outer layer, preferably of nonwoven material, closest to the user during use of the diaper, a liquid-tight outer layer, suitably of polyethylene, and an absorbent body disposed between the outer layers.

Disposable diapers now use almost exclusively tape tabs to tighten the diaper around the body of the user. Despite great efforts, diaper manufacturers have up to now not succeeded in designing tape fastening arrangements which fulfill all desires.

Since we are dealing with disposable products, it is necessary for reasons of economy that the liquid-impermeable outer layer of the diaper, which forms the rear of the diaper and usually consists of a plastic layer, be made very thin. This will of course adversely affect the strength of the layer.

Usually a very thin layer of polyethylene is used with very low tear strength. The tape tabs are with an end portion securely joined to the corners at one end of the diaper, and the opposite end portion of the tape tabs is provided with an adhesive the adhesive capacity of which must be relatively high in order to make it possible when putting the diaper on to fasten this tape portion using reasonable pressure to the liquid-impermeable outer layer at the other end of the diaper.

In practice it is proved necessary to use an adhesive the adhesive capacity of which exceeds the tear strength of the liquid-impermeable outer layer. This means in turn that it is practically impossible to correct an improperly put-on diaper or to inspect the diaper without tearing the plastic layer apart in attempting to loosen the tape.

A number of different attempts have been made to solve this problem. One method has been to reinforce the liquid-impermeable layer, which layer consists, as was mentioned above, usually of a thin polyethylene layer, which because of its low surface weight is easily stretched and tears when pulled. European Patent Application 9278 for example describes a diaper in which the plastic outer layer has been reinforced in the tape fastening zone with an adhesive coating applied to the inside thereof, said coating having a higher tensile strength and stretching less than the plastic layer.

It is true that one thereby achieves a diaper which, with respect to removal and refastening of tape, is better than diapers without reinforcement of the tape fastening zone, but nevertheless, this solution is still far from satisfactory. The adhesive capacity of the tape is higher than the tear strength of the plastic layer, which means that fragments of the plastic layer can be torn off and stick to the tape when it is removed. This means of course that the adhesive capacity of the tape when refastened will be less than what it was from the beginning.

A further significant disadvantage of fastening the tape directly to the thin polyethylene layer is that the adhesion will be poor. Since it is out of the question to press the tape hard against the plastic layer and thus against the infant, the adhesion will not be satisfactory, even though the tape per se has good adhesion. This is because of the fact that the thin plastic layer does not have a smooth surface but has an uneven surface. The thin polyethylene layer is not even initially smooth and even during the manufacturing of the diaper it is subjected to both pressure and heat treatment, causing additional surface unevenness. U.S. Pat. No. 4,067,337 describes another method of approaching the problem caused by the thin liquid-impermeable plastic outer layer. This patent specification reveals a tape attachment arrangement, in which the adhesive surface of the tape tabs has been divided into segments by means of a net applied on the adhesive surface itself. It is intended that the adhesion will be reduced thereby so that it will be less than the tear strength of the thin plastic layer. The disadvantage is of course that the adhesion of the tape tabs can be easily reduced to such a degree that the adhesion will be unsatisfactory.

In a fastening arrangement on the market for disposable diapers of the type in question, removal and refastening of the tape means is achieved by making the tape means of several separate tape tabs adhering to each other. The first tape tab used is designed to remain on the diaper plastic when the diaper is loosened and the next tape tab is used for refastening the diaper. A fastening arrangement constructed in this manner will however, for obvious reasons, be complicated and expensive to manufacture. Furthermore, the number of refastenings is limited by the number of tape tabs adhering to each other.

According to the present invention however, an arrangement for disposable diapers of the type described by way of introduction has been achieved which completely eliminates the above-mentioned disadvantages. It is characterized primarily in that at one end of the diaper there are tape tabs disposed in a manner known per se close to the corners of the diaper with a portion permanently joined to the liquid-tight outer layer at said diaper end, and that one or more plastic strips, for fastening the tape tabs when putting the diaper on the user, are mounted on the opposite end of the diaper and consist of a material which is inelastic and has suitable properties for fastening of the tape as well as removal and refastening thereof.

As regards the plastic reverse side of the diaper, several requirements must be fulfilled. It must be soft and comfortable for the user and, since it is a disposable product, it must be thin and inexpensive. It has previously not been possible to combine these requirements with good tape adhesion as well as good tape removal and refastening.

By arranging one or more plastic strips on the plastic backside of the diaper for fastening the tape tabs, this or these strip(s) can be entirely adapted to the desired characteristics of the tape tab fastening as regards strength and adhesion.

The adhesion between the tape tabs and the special plastic strip(s) according to the invention can also be adapted as desired. It must not however be greater than the cohesion of the adhesive if there is to be refastening capability. If one selects a smooth and even plastic strip, the adhesion will be great and one can then select tapes of lower quality than those used previously, making the product, the diaper, less expensive to manufacture.

The adhesion and refastening capacity of fastening tabs on a disposable diaper can thus now, by virtue of the invention, be optimized by selection of tape and type of plastic for the strip(s) to which the tape tabs are fastened, as well as by suitable treatment of the surfaces of the plastic strip(s). Attention must only be paid to adhesion and refastening. These characteristics can be easily controlled with advantage by for example different stamping of the plastic strip(s).

The plastic strip(s) can suitably be of material, preferably polyethylene or polypropylene, having a tear strength greater than that of the backside of the diaper plastic outer layer. By virtue of the fact that the plastic strip(s) according to the invention is(are) inelastic, there is no stretching when a tape tab attached thereto is pulled off.

A significant advantage over previously known fastening arrangements is that the tape tabs, by selecting surface smoothness of the plastic strip(s) can be given sufficient adhesive grip even if the tape tabs are only pressed very weakly against this(these) strip(s).

Figure 2:
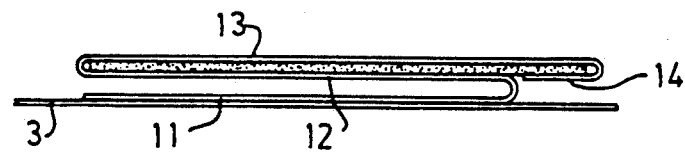
Figure 3:
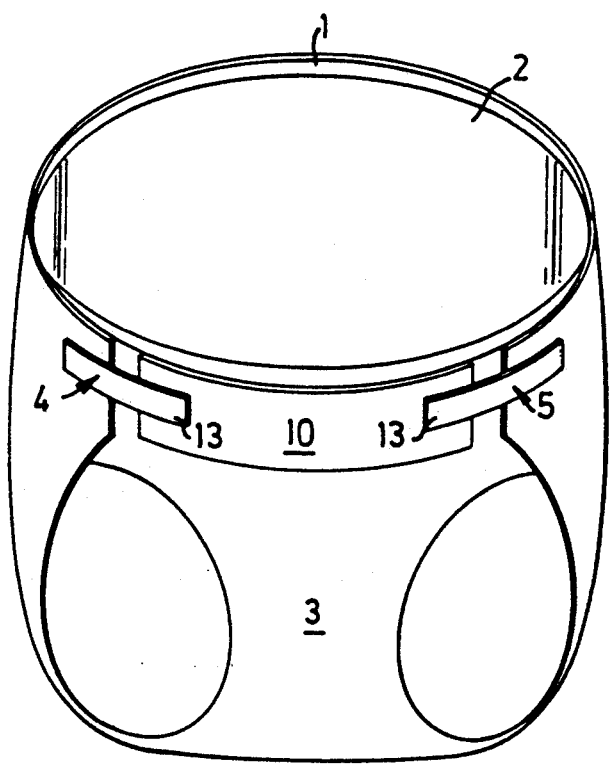

The invention will be described in more detail below with reference to an example which is shown in the accompanying drawings. FIG. 1 shows a diaper in a folded-out condition provided with an arrangement according to the invention. FIG. 2 shows a tape tab in a larger scale and FIG. 3 shows the diaper shown in FIG. 1 in its condition for use.

In FIG. 1, the absorbent body 1 has been indicated with dashed lines. It is surrounded by a liquid-permeable layer 2 of nonwoven textile which will be in contact with the user's body and by a liquid-tight thin layer 3 of polyethylene, which forms the backside of the diaper. The two layers 2,3 extend laterally outside the absorbent body and are joined there to each other.

The tape tabs 4,5 are permanently mounted with one end on the plastic layer 3 at one end 8, the rear end, of the diaper on the side flaps 6,7. At the opposite end 9 of the diaper, the front end, a nonelastic and smooth plastic strip 10 of polyester is mounted, which is glued securely to the liquid-tight layer 3 constituting the backside of the diaper.

FIG. 1 shows plastic strip 10 centrally mounted between the side edges of layer 3 at end 9 of the diaper, with its length less than the width of layer 3 at end 9 as well as at end 8.

FIG. 2 shows a tape tab in the folded-up condition before use. It has a first portion 11, which is coated with an adhesive and is permanently fixed to the plastic layer 3. The midportion 12 is however not coated with adhesive, but is instead coated with a release agent so that the third portion 13 of the tape flap, which is coated with adhesive, can, as shown at the Figure, be folded-in over the midportion 12 for detachable contact therewith. Finally, an end portion 14 of the tape tab is folded over itself to form a grip.

When the diaper is in the condition of use as shown in FIG. 3, the side flaps 6,7 of the rear end 8 of the diaper overlap the lateral portions of the front end 9 of the diaper. The third adhesive-coated tape portions 13 of the tape tabs 4,5 are pressed against the plastic strip 10 fixed to the backside of the front end of the diaper to fasten the diaper to the user. The adhesive tape portions 13 even with very little pressure, achieve a good grip on the smooth plastic strip, which can be a polyester strip for example. Since this plastic strip is inelastic, it does not stretch when the tape tabs are pulled off. The tape tabs can be easily removed without risk that the plastic strip will stretch and be broken, which is however a common occurrence in previously known diapers, where the tape tabs are fixed directly to the thin polyethylene layer serving as the backside to the diaper.

A suitable material for the plastic strip 10 is also polypropylene.

The manufacture of diapers provided with an arrangement according to the invention is suitably done with the diapers lying transversely to the manufacturing line, making it particularly easy to apply the plastic strip 10. It is then possible to allow it to extend across the entire front end 9 of the diaper so that the strip can be applied continuously. It is however not necessary that the thin polyethylene layer covers the entire backside of the diaper; rather it is sufficient that the plastic strip 10 and the polyethylene layer 3 overlap at the front end 9 of the diaper.

The plastic strip 10 serving as a fastening zone for the tape tabs 4,5 and extending over the front end of the diaper, will in practice function as a sort of belts for the diaper which is essentially only subjected to longitudinal stresses. It is thus not necessary to fix the strip 10 to the diaper along its entire surface.

In the example described above, the plastic strip for fastening of the tape tabs in accordance with the invention is assumed to have a smooth and even surface. This provides the strongest adhesion, but when one must also take into account tape quality and refastening possibilities, it can be suitable to emboss the plastic strip to obtain optimum characteristics.

What I claim is:

1. A disposable diaper which can be secured about a body of a user by means of pressure-sensitive adhesive tape tabs, said diaper having a first end having corners and a second end opposite said first end, comprising:

a liquid permeable inner layer closest to the user during use of the diaper;

a liquid-tight outer layer having an inner surface and an outer surface;

an absorbent layer disposed between the inner layer and the liquid-tight outer layer;

a pair of tape tabs at said first end of the diaper, each tape tab being positioned close to a respective one of said corners of said first end of the diaper with a first end portion of each of said tape tabs being permanently joined to the liquid-tight outer layer at said first end of said diaper; and a single elongated plastic strip comprising a material selected from the group consisting of polypropylene and polyester glued on said outer surface of said liquid-tight outer layer, adjacent said second end of said diaper, by glue between said outer surface and said plastic strip, said plastic strip having a length and an exposed plastic surface away from the user serving as a tape-receiving surface for releasably fastening the pair of tape tabs when putting the diaper on the user, said plastic strip comprising a material which has suitable properties for fastening of the pair of tape tabs thereto as well as easy removal of the tape tabs therefrom and refastening of the tape tabs thereto, without risk that the plastic strip will stretch and be broken by the removal of the tape tabs therefrom, said plastic strip being elongated transversely to the diaper to permit adjustment of tension of the diaper around the user by loosening at least one of said tape tabs from said plastic strip, adjusting a relative position of a thus-loosened tape tab and the plastic strip, and refastening the tape tab to said plastic strip in a thus-adjusted position, said liquid-tight outer layer being wider at said first end of the diaper than the length of said elongated plastic strip, each of said tape tabs having a width no greater than the width of the elongated plastic strip, each of said tape tabs having a second end portion opposite from its first end portion, each said second end portion having a pressure sensitive adhesive on a side thereof that contacts said plastic strip so that there is adhesion between said tape tabs and said plastic strip, whereby said plastic strip extends as a belt continuously between the tape tabs when the diaper is secured about the body of the user, said adhesive having a greater cohesion than said adhesion between said tape tabs and said plastic strip, and said plastic strip having a tear strength greater than said adhesion, whereby the combination of said liquid-tight outer layer, said plastic strip and said glue therebetween allows said tape tabs with said adhesive thereon to be releasable from and refastenable to said plastic strip without stretching and breaking said plastic strip.

2. A disposable diaper as claimed in claim 1, wherein said single plastic strip is inelastic.

3. A disposable diaper which can be secured about a body of a user by means of pressure-sensitive adhesive tape tabs, said diaper having a first end having corners and a second end opposite said first end, comprising:

a liquid permeable inner layer closest to the user during use of the diaper;

a liquid-tight outer layer having an inner surface and an outer surface;

an absorbent layer disposed between the inner layer and the liquid-tight outer layer;

a pair of tape tabs at said first end of the diaper, each tape tab being positioned close to a respective one of said corners of said first end of the diaper with a first end portion of each of said tape tabs being permanently joined to the liquid-tight outer layer at said first end of said diaper; and a single elongated plastic strip comprising a material selected from the group consisting of polypropylene and polyester glued on said outer surface of said liquid-tight outer layer, adjacent said second end of said diaper, by glue between said outer surface and said plastic strip, said plastic strip having an exposed plastic surface away from the user serving as a tape-receiving surface for releasably fastening the pair of tape tabs when putting the diaper on the user, said plastic strip comprising a material which has suitable properties for fastening of the pair of tape tabs thereto as well as easy removal of the tape tabs therefrom and refastening of the tape tabs thereto, without risk that the plastic strip will stretch and be broken by the removal of the tape tabs therefrom, said plastic strip being elongated transversely to the diaper to permit adjustment of tension of the diaper around the user by loosening at least one of said tape tabs from said plastic strip, adjusting a relative position of a thus-loosened tape tab and the plastic strip, and refastening the tape tab to said plastic strip in a thus-adjusted position, said elongated plastic strip being mounted centrally of said second end of the diaper, and being shorter than a transverse extent of said liquid-tight outer layer at said second end of the diaper, each of said tape tabs having a width no greater than the width of the elongated plastic strip, each of said tape tabs having a second end portion opposite from its first end portion, each said second end portion having a pressure sensitive adhesive on a side thereof that contacts said plastic strip so that there is adhesion between said tape tabs and said plastic strip, whereby said plastic strip extends as a belt continuously between the tape tabs when the diaper is secured about the body of the user, said adhesive having a greater cohesion than said adhesion between said tape tabs and said plastic strip, and said plastic strip having a tear strength greater than said adhesion, whereby the combination of said liquid-tight outer layer, said plastic strip and said glue therebetween allows said tape tabs with said adhesive thereon to be releasable from and refastenable to said plastic strip without stretching and breaking said plastic strip.

* * * * *